(12) United States Patent
Stoddard et al.

(10) Patent No.: US 8,768,497 B2
(45) Date of Patent: Jul. 1, 2014

(54) TREATING CLEFT PALATE

(75) Inventors: Philip B. Stoddard, Tampa, FL (US); Beth A. Roscoe, Tampa, FL (US)

(73) Assignee: Shriners Hospitals for Children, Tampa, FL (US)

( * ) Notice: Subject to any disclaimer, the term of this patent is extended or adjusted under 35 U.S.C. 154(b) by 811 days.

(21) Appl. No.: 12/867,171

(22) PCT Filed: Feb. 27, 2009

(86) PCT No.: PCT/US2009/035478
§ 371 (c)(1),
(2), (4) Date: Nov. 8, 2010

(87) PCT Pub. No.: WO2009/111310
PCT Pub. Date: Sep. 11, 2009

(65) Prior Publication Data
US 2011/0060438 A1    Mar. 10, 2011

Related U.S. Application Data

(60) Provisional application No. 61/032,928, filed on Feb. 29, 2008.

(51) Int. Cl.
*G06F 19/00* (2011.01)
*A61C 3/00* (2006.01)

(52) U.S. Cl.
USPC .................. 700/98; 700/118; 433/2; 433/24; 433/34; 623/17.18; 703/11

(58) Field of Classification Search
USPC .......... 700/98, 118; 433/2, 24, 34; 623/17.18; 703/11
See application file for complete search history.

(56) References Cited

U.S. PATENT DOCUMENTS

| | | | |
|---|---|---|---|
| 4,195,046 A * | 3/1980 | Kesling ............................ | 264/16 |
| 4,842,515 A * | 6/1989 | Zeiser .............................. | 433/74 |
| 6,882,894 B2 | 4/2005 | Durbin et al. | |
| 7,192,273 B2 | 3/2007 | McSurdy, Jr. | |
| 2005/0177261 A1* | 8/2005 | Durbin et al. ................... | 700/98 |
| 2005/0186524 A1 | 8/2005 | Abolfathi et al. | |
| 2008/0153061 A1* | 6/2008 | Marcello ........................ | 433/173 |
| 2008/0305453 A1* | 12/2008 | Kitching et al. ................ | 433/24 |

OTHER PUBLICATIONS

International Preliminary Report on Patentability; PCT/US2009/035478; mailed Sep. 10, 2010.

* cited by examiner

*Primary Examiner* — Mohammad Ali
*Assistant Examiner* — Sheela S Rao
(74) *Attorney, Agent, or Firm* — Fish & Richardson P.C.

(57) ABSTRACT

The present application describes, inter alia, methods, devices, and systems for modeling and fabricating corrective appliances and methods of treating cleft palate using same.

12 Claims, 10 Drawing Sheets

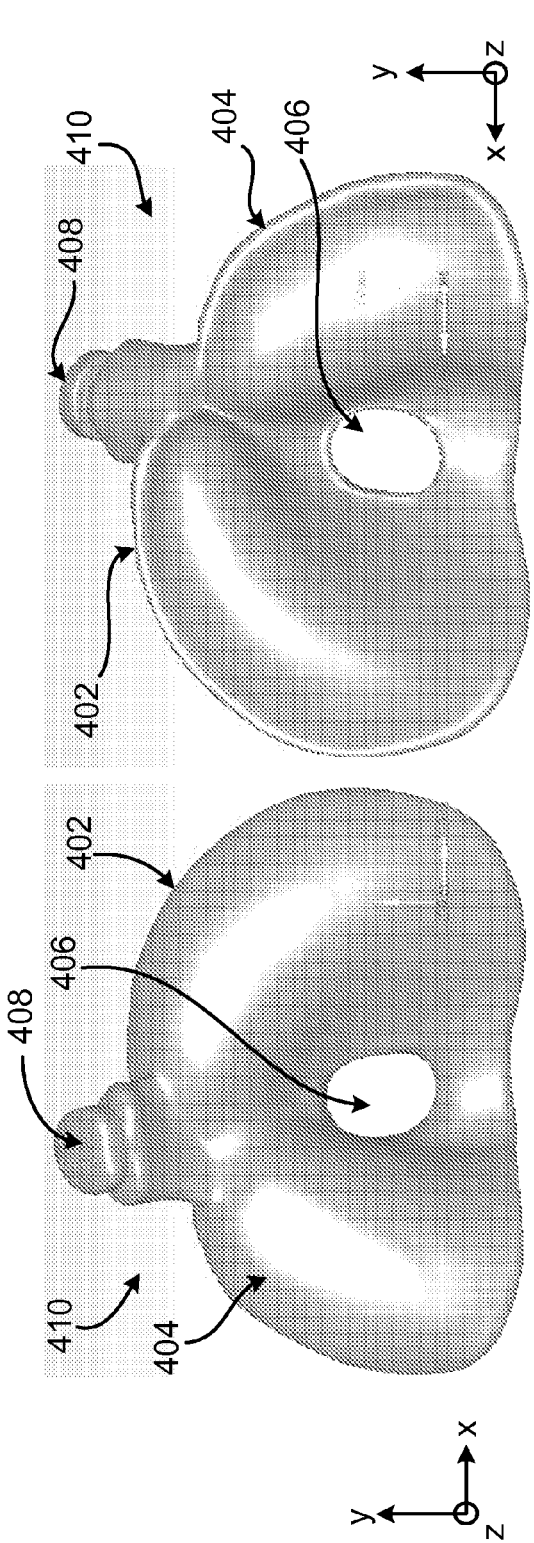
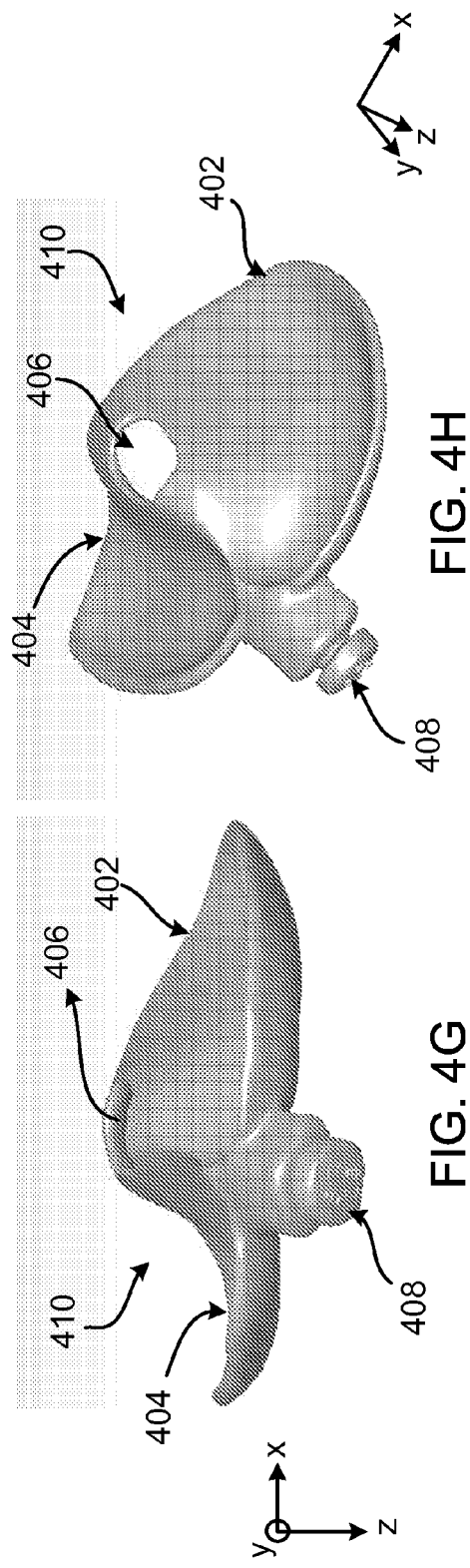
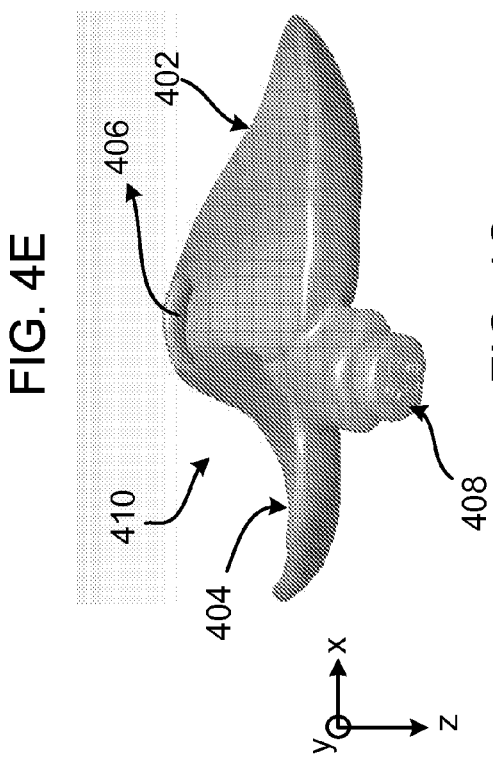
FIG. 4E
FIG. 4F
FIG. 4G
FIG. 4H

TREATING CLEFT PALATE

CROSS REFERENCE TO RELATED APPLICATIONS

This application is the National Stage of International Application No. PCT/US2009/035478, filed Feb. 27, 2009, which claims priority to U.S. Provisional No. 61/032,928, filed on Feb. 29, 2008, the contents of each of which are incorporated herein by reference in their entirety.

TECHNICAL FIELD

This invention relates to the treatment of cleft palate malformations.

BACKGROUND

The palate forms the arched roof of the mouth and the floor of the nasal cavities. The hard palate is a concave structure whose anterior two-thirds has a skeleton formed by the palatine processes of the maxillary and the horizontal plates of the palatine bones. A common congenital deformity is cleft palate, in which the maxillary segments of the palate do not fuse properly during embryonic and fetal development. The cleft may involve only the uvula, or may extend through the soft and hard regions of the palate, and may also include a cleft of the gum and the lip. This invention pertains to, inter alia, the treatment of wide cleft lip and palate. A cleft palate may be unilateral complete, unilateral incomplete, bilateral complete, bilateral incomplete, or mid-line. The embryological basis of cleft palate is failure of the mesenchymal masses in the lateral palatine processes to meet and fuse with each other, with the nasal septum, or with the posterior margin of the median palatine process.

An estimated 7,500 children are born in the United States each year with cleft lip, cleft palate, or both. In addition to having a facial disfigurement, children with cleft palate may also suffer from eating, speaking, or hearing abnormalities. Pre-surgical orthopedic treatment of cleft palate malformations reduces the distance between the maxillary segments. This treatment facilitates subsequent soft-tissue repair, as, for example, the lip repair will be under less tension than it would have been without treatment. One existing method of pre-surgical treatment uses the Latham dentomaxillary appliance (DMA), which is pinned to the subject's palatal bone segments while the subject is under general anesthesia. The DMA appliance is adjusted daily. Another method uses the naso-alveolar molding (NAM) device (by Grayson and Cutting), in which a removable acrylic plate is modified manually by orthodontists at weekly intervals.

SUMMARY

Provided herein are, e.g., methods of modeling a planned reconstruction of a cleft palate. The purpose of the methods is to, inter alia, achieve a narrower distance between a patient's maxillary segments at the conclusion of treatment, while concurrently accommodating growth of the patient. In general, the methods include obtaining a three-dimensional digital model that represents the initial shape of the palate. The digital model can be edited to create a digital model of the final shape of the palate at the conclusion of treatment. A digital model of at least one intermediate shape of the palate can be created by interpolating between the initial shape and the final shape. In some instances, the digital model of the final shape can be adjusted to account for an anticipated growth of the palate during a period.

Digital models of corrective appliances can be created, which are digital representations of appliances designed to, e.g., engage a patient's palate in accordance with the planned reconstruction and progressively narrow the distance between a patient's maxillary segments while accommodating the growth of a patient's palate. The digital models of corrective appliances are digital representations of appliances adapted to engage, e.g., the initial shape, the final shape and the intermediate shapes of the palate, as represented by digital models of cleft palates described herein. The digital model of the corrective appliance can include a first region that engages a first maxillary segment of the cleft palate (e.g., the major maxillary segment of a unilateral cleft palate) and a second region that engages a second maxillary segment of the cleft palate (e.g., the minor maxillary segment of a unilateral cleft palate); the first and the second regions being separated by a distance. One or more further digital models of corrective appliances may be created, and need not be created in any particular order. For example, if a first digital model of a corrective appliance is created to engage the final shape of the palate, a digital model of a second corrective appliance can be created, wherein the distance in the first digital model of the corrective appliance is less than a distance in the second appliance. Likewise, if a first digital model of a corrective appliance is created to engage the initial shape of the palate, a digital model of a second corrective appliance can be created, wherein the distance in the first corrective appliance is greater than the distance in the second appliance. The distance in the model of the corrective appliance that is adapted to engage the final shape of the palate can be specified by a health care provider. In some instances, the specified distance can be, e.g., between two and three millimeters or between one and two millimeters or no more than one millimeter (e.g., the regions may be touching each other). When applying fabricated versions of the appliances to patients to treat the patient's cleft palate, skilled practitioners will appreciate that the appliance adapted to fit the initial shape of the cleft palate, which has the greatest distance between regions, is administered first, followed by administration of appliances adapted to fit intermediate shapes of the cleft palate. The appliance adapted to fit the final shape of the cleft palate is administered last and comprises the least distance between the major and minor maxillary segments. A model of a strut to engage the nasal ala can be added to a digital model of the appliance. The strut can be incorporated into the unitary structure of the appliance, with the position of the strut varying from one appliance to the next. This can allow for correction of the cleft, growth of the palate and gradual elevation of the nostril, simultaneously.

In the case of bilateral complete cleft lip and palate, the digital model of a corrective appliance includes a first region that engages a first maxillary segment of the cleft palate (e.g., one maxillary segment in a bilateral cleft palate model), a second region that engages a second maxillary segment of the cleft palate (e.g., the contralateral maxillary segment in a bilateral cleft palate), and a third region that engages the premaxilla; the first region and the premaxilla being separated by a first distance and the second region and the premaxilla being separated by a second distance. One or more further digital models of corrective appliances may be created, and need not be created in any particular order. For example, if a first digital model of a corrective appliance is created to engage the final shape of the palate, a second corrective appliance can be created, wherein both the first distance and the second distance in the first corrective appliance are less than a first distance and a second distance, respectively, in the second appliance. Likewise, if a first digital model of a corrective appliance is created to engage the initial shape of the palate, a second corrective appliance can be created, wherein both the first and second distances in the first corrective appliance are greater than the first distance and second distance, respectively, in the second appliance. The first and second distances in the model of the corrective appliance that is adapted to engage the final shape of the palate can each be specified by a health care provider. In some instances, the specified distance can be between two and three millimeters or between one and two millimeters or no more than one millimeter (e.g., one or both regions may be touching the premaxilla). A model of at least one strut, e.g., two struts, to engage the nasal ala can be added to a digital model of the appliance. The strut can be incorporated into the unitary structure of the appliance with the position of the strut varying from one appliance to the next. This allows for correction of the cleft, growth of the palate and gradual elevation of the nostril, simultaneously.

The number of intermediate shapes can be between 2 and 20, e.g., between 12 and 15, inclusive. The model of the corrective appliance can include at least one retention post, an air hole, and/or a nasal strut(s).

Also described herein are methods of fabricating a corrective appliance. In such methods, a three-dimensional digital model can be obtained of an initial shape of a cleft palate. The digital model can be edited to create a digital model of a final shape of the palate which can, e.g., incorporate cleft correction and/or anticipated growth and/or gradual elevation of the nostril during treatment. A digital model of at least one intermediate shape of the palate can be created by interpolating between the initial shape and the final shape. At least one digital model can be created of a corrective appliance, adapted to engage the initial, the final, or the intermediate shape(s) (e.g., of a unilateral cleft palate), that includes a first region that engages a first maxillary segment of the cleft palate (e.g., the major maxillary segment in a unilateral cleft palate), and a second region that engages a second maxillary segment of the cleft palate (e.g., the minor maxillary segment in a unilateral cleft palate), wherein the first and the second regions are separated by a distance. The appliance can be fabricated from the digital model using an automated manufacturing technique, e.g., rapid prototyping. One or more further corrective appliances may be fabricated, and need not be fabricated in any particular order. For example, if a first corrective appliance is fabricated to engage the final shape of the palate, a second corrective appliance can be fabricated, wherein the distance in the first corrective appliance is less than a distance in the second appliance. Likewise, if a first corrective appliance is fabricated to engage the initial shape of the palate, a second corrective appliance can be fabricated, wherein the distance in the first corrective appliance is greater than the distance in the second appliance. In some instances, the distance in the model of the corrective appliance that is adapted to engage the final shape of the palate is specified by a health care provider. In some instances, the specified distance can be, e.g., between two and three millimeters or between one and two millimeters or no more than one millimeter (e.g., the regions may be touching each other).

In some instances (e.g., for a bilateral cleft palate), at least one digital model is created of a corrective appliance, adapted to engage the initial, the final, or the intermediate shape, that includes a first region that engages a first maxillary segment of the cleft palate (e.g., one maxillary segment of a bilateral cleft palate), a second region that engages a second maxillary segment of the cleft palate (e.g., the contralateral maxillary segment of a bilateral cleft palate), and a third region that engages the premaxilla of the cleft palate, in which the first region and the premaxilla are separated by a first distance and the second region and the premaxilla are separated by a second distance. The appliance can be fabricated according to the digital model using an automated manufacturing technique, e.g., rapid prototyping. One or more further corrective appliances may be fabricated, and need not be fabricated in any particular order. For example, if a first corrective appliance is fabricated to engage the final shape of the palate, a second corrective appliance can be fabricated, wherein both the first distance and the second distance in the first corrective appliance are less than a first distance and a second distance, respectively, in the second appliance. Likewise, if a first corrective appliance is fabricated to engage the initial shape of the palate, a second corrective appliance can be fabricated, wherein the first distance and second distance in the first corrective appliance is greater than the first and second distances in the second appliance. The first and second distances in the model of the corrective appliance that is adapted to engage the final shape of the palate can in some instances each be specified by a health care provider. In some instances, the specified distance can be, e.g., between two and three millimeters or between one and two millimeters or no more than one millimeter (e.g., one or both regions may be touching the premaxilla).

Any number of intermediate shapes can be generated and used. The number of intermediate shapes can be, e.g., between 2 and 20, e.g., 12 and 15. A digital model or fabricated version of a corrective appliance described herein can include at least one retention post, at least one strut, and/or an air hole.

Also described herein is a group of corrective appliances, each adapted to engage a shape of a cleft palate, e.g., a unilateral, bilateral, or mid-line cleft palate. Appliances in the group can be fabricated in any order. The appliances can include a first region configured to engage a first maxillary segment (e.g., a major maxillary segment) of the cleft palate and a second region configured to engage a second maxillary segment (e.g., a minor maxillary segment) of the cleft palate. The first and the second regions are separated by a distance. The distance in one appliance can be different (i.e., less or greater) than a distance in a second appliance in the group. A strut can be included which is adapted to engage the nasal ala.

Alternatively or in addition, members of the group of corrective appliances can each be adapted to engage a cleft palate, e.g., a bilateral cleft palate. An appliance would typically include a first region configured to engage a first maxillary segment of the cleft palate, a second region configured to engage a second maxillary segment of the cleft palate, and a third region configured to engage the premaxilla of the cleft palate. The first region and the premaxilla can be separated by a first distance and the second region and the premaxilla can be separated by a second distance. At least one distance (e.g., both distances) in one appliance can be different (i.e., less or greater) than a distance in a second appliance in the group. At least one strut, e.g., two struts, can be included which is adapted to engage the nasal ala.

Also described herein are kits that include, e.g., two or more corrective appliances described herein (e.g., appliances adapted to engage a bilateral, unilateral, or mid-line cleft palate). For example, each appliance may include a first region that engages a first (e.g., major) maxillary segment of a cleft palate and a second region that engages a second (e.g., minor) maxillary segment of a cleft palate. The first and the second regions can be separated by a distance in one appliance that is different (i.e., less or greater) than a distance in a second appliance in the kit. Alternatively or in addition, a kit can include two or more corrective appliances, each appliance including a first region that engages a first maxillary segment of the cleft palate, a second region that engages a second maxillary segment of the cleft palate, and a third region that engages the premaxilla of a cleft palate. The first region and the premaxilla can be separated by a first distance and the second region and the premaxilla can be separated by a second distance. At least one distance (e.g., both distances) in one appliance in the group can be different (i.e., less or greater) than a distance in a second appliance in the kit. At least one strut, e.g., two struts, can be included which is adapted to engage the nasal ala.

Corrective appliances described herein can be constructed of any type of material useful in the art, e.g., a material comprising methyl methacrylate and/or nylon.

Also described herein is a computer program product, encoded on a computer-readable medium, operable to cause a data processing apparatus to perform operations. The operations can include obtaining a three-dimensional digital model representing an initial shape of a palate, editing the digital model to create a digital model of a final shape of the palate, and interpolating between the initial shape and the final shape to create a digital model of at least one intermediate shape of the palate. The computer program product can be operable to cause a data processing apparatus to perform operations that include adjusting the final shape to account for an anticipated growth during the treatment period. The operations can include creating the digital models of corrective appliances described herein.

Also provided herein are methods of treating cleft palate (e.g., a unilateral, bilateral or mid-line cleft palate). In such methods, a three-dimensional digital model can be obtained of an initial shape of a palate. The digital model can be edited to create a digital model of a final shape of the palate. A digital model of at least one intermediate shape of the palate can be created by interpolating between the initial shape and the final shape. Digital models of corrective appliances can be created as described herein. Appliances can be fabricated according to the digital models by hand (e.g., using art-known methods, e.g., by making a mold by hand and forming the appliance) or using an automated manufacturing technique, e.g., rapid prototyping, as described herein. Each member of the fabricated group of appliances can be applied to a patient to thereby treat cleft palate. For example, a fabricated appliance that fits the initial shape of a cleft palate can be applied to the patient, followed by appliances that fit intermediate shapes of the cleft palate. Lastly, an appliance that fits the final shape of the cleft palate is applied to the patient.

A three-dimensional model of the palate may be obtained, e.g., by taking an impression of the cleft palate forming a negative model of the palate, making a positive model of the palate from the negative model, and optionally creating a check plate. The fit of the check plate can optionally be tested on a patient. A model, e.g., a positive plaster model, of the palate can be scanned in three dimensions. The scanned data can be read into a three-dimensional modeling program. Alternatively or in addition, the impression (e.g., negative model) can be scanned directly, i.e., without forming a positive model. Alternatively or in addition, a patient can be scanned directly, e.g., using a three-dimensional and/or a series of two-dimensional biomedical imaging scans.

Any number of intermediate shapes between the initial and final palate shapes can be generated and used. The number of intermediate shapes can be, e.g., between two and 20, e.g., 12 and 15. The model of a corrective appliance can further include at least one retention post and/or an air hole, and/or nasal strut(s).

The automated manufacturing technique can include rapid prototyping. In some instances, the specified distance(s) can be between two and three millimeters or between one and two millimeters or no more than one millimeter. The distance(s) in the model of the corrective appliance that is adapted to engage the final shape of the palate can be specified by a health care provider. A material used to form the group of fabricated appliances can include methyl methacrylate and/or nylon.

A corrective appliance described herein can include (e.g. be coated with and/or contain within the corrective appliance) a substance that is to be administered to the patient, e.g., a substance that enhances a property of the appliance and/or is beneficial to the patient. For example, the appliance can include an anesthetic, an antiseptic, and/or a stimulator of growth, among many other possible substances. An appliance can be fabricated such that the substance is released to the patient in any desirable fashion, e.g., rapidly or slowly over time.

These general and specific aspects can be implemented using a system, a method, or a computer program, or any combination of systems, methods, and computer programs.

The details of one or more embodiments of the invention are set forth in the accompanying drawings and the description below.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. The materials, methods, and examples are illustrative only and not intended to be limiting.

Other features, objects, and advantages of the invention will be apparent from the description and drawings, and from the claims.

DESCRIPTION OF DRAWINGS

FIGS. 4A-4J are views of digital models of exemplary corrective appliances. FIGS. 4A-4D are views of a digital model of an exemplary corrective appliance adapted to engage an early-shape of a patient's cleft palate. FIGS. 4E-4H are views of a digital model of an exemplary corrective appliance adapted to engage a late-shape of a patient's cleft palate. FIG. 4I is a superimposed palate-side view of the exemplary corrective appliances of FIGS. 4B and 4F. FIG. 4J is a view of a digital model of an exemplary corrective appliance comprising a nasal strut.

FIG. 5A illustrates a digital model of a corrective appliance. FIG. 5B is a photograph of a patient wearing the appliance created from the digital model.

FIG. 6A shows the patient's cleft palate before treatment (e.g., with an initial shape of the cleft palate). FIG. 6B shows the patient's cleft palate at an intermediate stage of treatment. FIG. 6C shows the patient's cleft palate at a later stage of treatment.

FIG. 7A is a photograph of the patient five days after surgery. FIG. 7B is a photograph of the patient two weeks after surgery.

DETAILED DESCRIPTION

Current methods for reducing the separation between maxillary segments of patients with cleft-palate require a health care professional (e.g., an orthodontist or a plastic surgeon) to repeatedly (e.g., daily, weekly, or monthly) adjust a corrective appliance. This gradual correction by manual methods, such as a parent turning a screw for the Latham device or a health care professional manually grinding and adding material for the NAM device, allows for variable results among patients.

This application describes the use of advanced computer modeling to assist in the creation of a series of corrective appliances to reposition segments of a cleft palate (e.g., a bilateral complete cleft palate or a unilateral complete cleft palate) in a patient (e.g., a newborn). The modeling can be performed for a patient and the design can be adjusted to account for, inter alia, growth of the maxilla during the treatment period. As a result, fewer trips or shorter trips or both to a health care provider are needed, more standardized results can be achieved, and a correction that accommodates the patient's growth can be performed in a more controlled fashion by a health care provider.

The term "patient" is used throughout the specification to describe an animal, human or non-human, to whom treatment according to the methods of the present invention is provided. Veterinary and non-veterinary applications are contemplated. Exemplary subjects are humans, e.g., children, such as infants.

As used herein, "treatment" relates to any manner in which the severity of a cleft palate is ameliorated or otherwise beneficially altered. As used herein, "amelioration of the symptoms of a particular disorder" refers to any lessening, whether permanent or temporary, lasting or transient, that can be attributed to or associated with a treating of a patient using an appliance or a method or both as described in this application.

Cleft Palate Modeling

Figure 1:
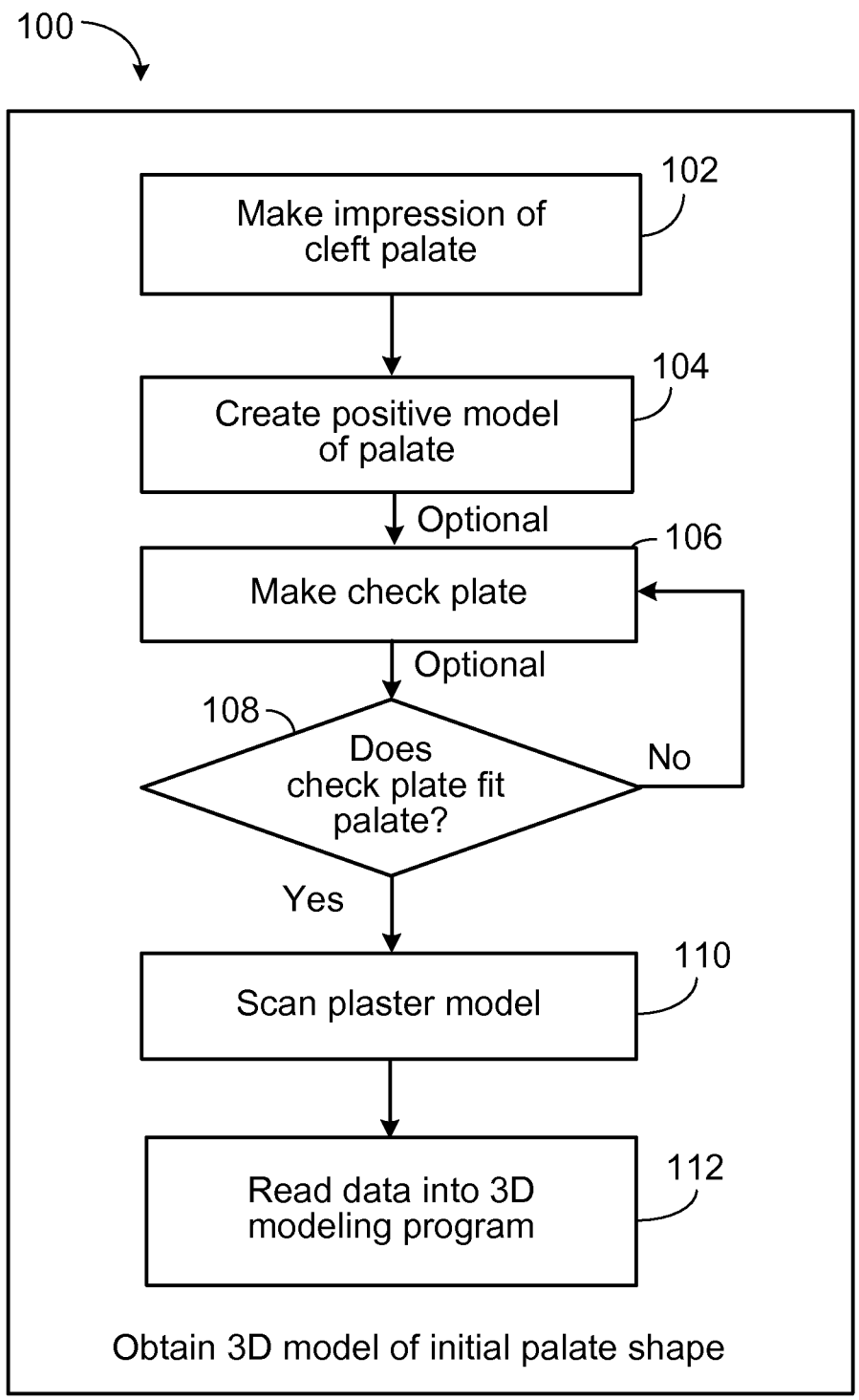
FIG. 1 is a flowchart that illustrates an exemplary procedure for obtaining a digital three-dimensional cleft palate model.
Figure 2:
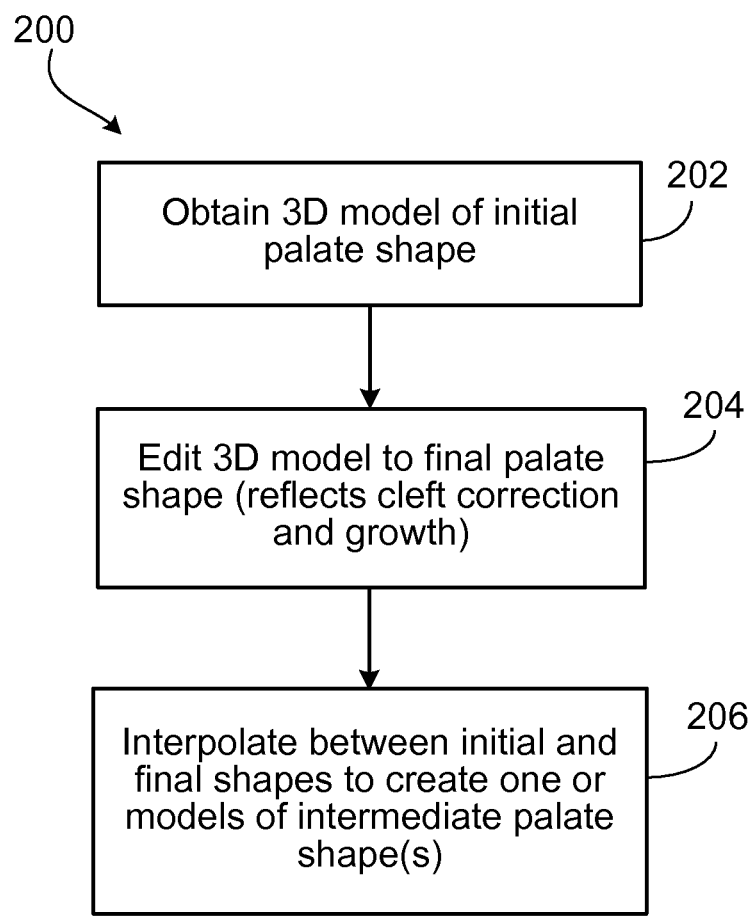
FIG. 2 is a flowchart illustrating an overview of exemplary steps for creating digital cleft palate models.

The present invention provides, inter alia, methods for modeling a patient's cleft palate. The flowchart 100 in FIG. 1 provides an overview of how a practitioner might obtain a three-dimensional model of a cleft palate. The flowchart 200 in FIG. 2 provides an overview of how a practitioner might create digital models of patient's cleft palate. Generally, to obtain 202 a three-dimensional model of an initial palate shape, a health care provider (e.g., an orthodontist, a dental assistant, or a plastic surgeon) can, for example, make an impression, create a plaster positive model and scan; make an impression and scan; or scan the patient directly, to generate a software-implemented rendering of the initial cleft palate, with the initial separation between maxillary segments (in the case of a unilateral cleft) or between the maxillary segments and the premaxilla (in the case of bilateral cleft). To edit 204 the three-dimensional model, the provider can, e.g., physically or digitally reshape the model to achieve a remodeled, final palate shape at the conclusion of treatment that has a smaller separation between the maxillary segments (in the case of a unilateral cleft) or between the maxillary segments and the premaxilla (in the case of bilateral cleft), and, e.g., reflects the growth of the patient's palate during the treatment period. To interpolate 206 between the initial and final palate shapes, the provider can, for example, use a three-dimensional graphical rendering program to create a model of intermediate palate shape(s).

Referring to FIG. 1 and describing an embodiment of methods described herein in further detail, modeling can begin with a health care provider making 102 a palatal impression of a patient's palate using a commercially-available dental impression material, e.g., Coltene Rapid Soft™ or Jeltrate®. The negative impression can be used to create 104 a positive model of the palate and can be constructed from any material useful for such a procedure, for example, plaster, dental stone, gypsum. The health care provider can optionally make 106 a "test plate" by heating a thickness (e.g., one-eighth of an inch) of thermo-formable plastic such as Surlyn® or Durplex®/Vivak® resin (e.g., polyphenylene ether (PPE), polycarbonate (PC), or ethylene methacrylic acid) to a temperature above the material's glass transition temperature but below its melting temperature (e.g., between 165° F. and 240° F. for PPE or between 300° F. and 510° F. for PC). While in a molten condition, the thermoplastic can be shaped into a desired shape using any art-known technique, e.g., extrusion, injection molding, compression molding, blow molding, film blowing, fiber spinning, blown fiber, spunbonded fiber coextrusion, paper coating, calendering, rotational molding, casting, or vacuum thermoforming, e.g. drape forming or bubble forming. The shapes so formed can be subsequently cooled to set the shape and induce crystallization. They can then be trimmed and finished using art-known techniques.

A health care provider (e.g., a plastic surgeon) can optionally check 108 to determine whether the plate fits the palate of the patient by placing the plate in the patient's mouth. Any adjustments necessary can be made to this check plate to achieve an ideal custom fit. If a modification of the plate is needed, a health care provider (e.g., an orthodontist) can create 104 another positive model from the adjusted check plate.

Methods for making and using thermoplastic compositions are well known to those of skill in the art. Skilled practitioners will appreciate that the above-described steps can be used with any thermoplastic or thermoset plastic (or mixtures of such thermoset plastics, e.g., mixtures of at least two, e.g., at least three, four, five, seven, or 10 thermoset plastics), regardless of whether the thermoplastic or thermoset plastic is natural or synthetic, or biodegradable or non-biodegradable. Further, as is known to skilled practitioners, a thermoset plastic composition can contain one or more additive, e.g., a filler, a plasticizer, an antioxidant, an ultraviolet stabilizer, a lubricant or a slip agent, a pigment, a trans-esterification catalyst or another cross linking agent, a flame retardant, or an antistatic agent.

Skilled practitioners will appreciate that there are various art known methods for obtaining a three-dimensional representation of an object (e.g., a palate). For example, a commercially-available, three-dimensional scanner can be used to obtain a digital representation of the physical model of the palate. The scanner used can be a contact scanner (e.g., a coordinate measuring machine) or a non-contact, active scanner, i.e., one that emits radiation and detects reflected radiation to infer topography (e.g., a time-of-flight range finder, a triangulation range finder, a conoscopic hologram, a projection of structured or modulated light, or an optical laser scanner), or a non-contact, passive scanner that infers topography based on the compilation of two-dimensional images taken at multiple angles. The scanner can capture 110 the three-dimensional surface anatomy of the palate at the beginning of treatment from the positive model 104. The scanner can be calibrated to a particular resolution and set to obtain a specified number of data points (e.g., 500, 1,000, 5,000, 20,000, or more). The scanner data can be in the form of a "point cloud," or a series of spatial coordinates (e.g., x, y, and z coordinates) representing the topography of the cleft palate. The points of the point cloud define the shape of the palate but do not occupy any space.

In some embodiments, a digital representation of a three-dimensional model of the palate can be obtained directly from a series of two-dimensional biomedical imaging scans (e.g., magnetic resonance imaging or computed tomography) or one three-dimensional biomedical imaging scan (e.g., intraoral scan, magnetic resonance imaging, or computed tomography) of the patient.

Data representative of the three-dimensional topography of the cleft palate (e.g., a point cloud representative of the physical model of the palate, a DICOM file of the tomography of the patient's palate, or a reconstruction of the patient's palate based on a DICOM file) can be transferred 112, for example, from the scanner into a commercially-available software package (e.g., AutoCAD®, Geomagic Studio®, or TurboCAD®)

A surface model of the palate can be constructed from the data (e.g., a point cloud, an IGES file, a DICOM file, or a reconstruction from a DICOM file) in the three-dimensional modeling program that represents the initial shape of the palate. The surface can be edited 204 (e.g., by a user and/or by an automated system) to bring the separate maxillary segments together into the desired palate shape. Models of the maxillary segments can be manipulated to achieve a more ideal dental arch configuration, i.e., a "final" shape of the palate at the conclusion of the treatment.

The final palate surface model can be scaled to account for an anticipated growth during a treatment period (e.g., four months, six months, or a year). The amount of growth can be forecast based on the patient's birth length, head circumference, gestational age and anthropometric standards. A health care provider (e.g., an oral and maxillofacial surgeon, an orthodontist, or a plastic surgeon) can review the final surface model for accuracy and can determine how the palatal segments should be positioned at the conclusion of the treatment period.

Generally, as used herein, an "initial shape" refers to the initial shape of a patient's untreated cleft palate. As used herein, a "final shape" refers to the shape of a patient's treated cleft palate. A "treated" cleft palate can have a cleft that is reduced to any extent. Typically, the final shape of the palate is closer to a biologically non-cleft palate and is more receptive to surgery.

Optionally, from the initial and the final polygon surface models, an appropriate number (e.g., as prescribed by a program or by a health care provider) of intermediate digital models can be interpolated 206 to gradually narrow the original cleft or clefts (e.g., to a distance specified by a health care provider). The number of steps may be at least two steps, e.g., at least three, four, five, six, 12, 15, 18, 20, or more. Skilled practitioners will appreciate that any number of models can be used. These intermediate models represent the gradual three-dimensional progression of the palate during therapy.

Figure 3:
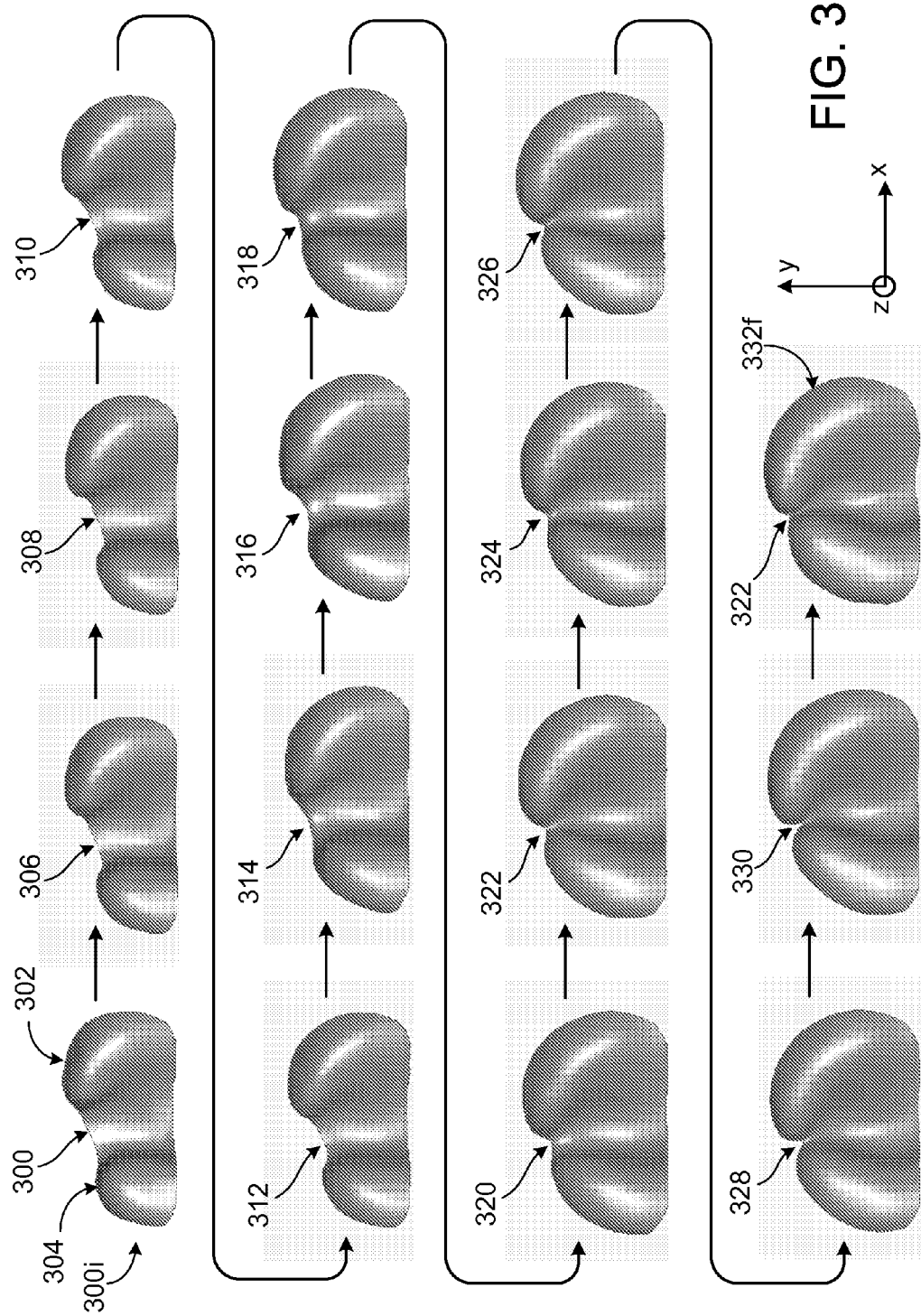
FIG. 3 illustrates a series of digital models of a cleft palate created in accordance with the present invention.

FIG. 3 shows a projected evolution of a series of digital models of a unilateral complete cleft palate from an initial shape 300i to a remodeled, final state 332f. In this example, the initial palate shape 300i has a separation 300, for example, about 15 mm, between maxillary segments 302 and 304. The final palate shape 332f has a separation 332, for example, about 2 mm, that is less than the separation 300. A series of intermediate shapes have separations 306, 308, 310, 312, 314, 316, 318, 320, 322, 324, 326, 328, and 330, that are each smaller than separation 300 and greater than separation 332. The spatial axes shown (i.e., the x, y, and z axes) correspond to the spatial axes of the patient; the spatial origin is located at the midpoint between the maxillary tuberosities. The z axis, which is perpendicular to the plane of FIG. 3 (i.e., increasing z values are coming out of the page, denoted by a circled dot), measures the cephalad-caudad axis of the patient; higher z values correspond to a more caudad position of the patient. The y axis measures the dorso-ventral (i.e., back-to-front) axis of the patient; higher y values correspond to a more ventral position of the patient. The x axis measures the medio-lateral axis of the patient; higher x values correspond to a more lateral position of the patient that is farther from his midline. The x-y plane corresponds to the occlusal plane of the patient. A separation 300 (e.g., about 15 mm) between the maxillary segment 302 and the maxillary segment 304 is maximal; this separation narrows progressively with each intermediate digital model and attains a minimal value in the final separation 332. The final separation is predetermined, for example, by a health care professional, and will depend on the circumstances of the patient (e.g., planned surgeries). The final distance can be, e.g., no more than one millimeter or, in the case of a planned gingivoperiosteoplasty, the final distance can be between two and three millimeters, e.g., to allow "room" for performing surgery.

Likewise, the projected evolution for a digital model of a bilateral complete cleft palate (as explained above for a unilateral complete cleft palate) can be obtained. A digital model of a bilateral complete cleft palate can have a first separation between a maxillary segment and a premaxilla and a second separation between a second maxillary segment and the premaxilla. Both the first separation and the second separation will narrow progressively with each intermediate model; each separation will attain a minimal value in a final digital model of the bilateral complete cleft palate.

In some embodiments, the projected evolution for a digital model of a cleft palate can also include a digital model of the position of the patient's nose relative to a position of the palate.

Corrective Appliance Modeling

The digital palatal model corresponding to each of the initial, final, and intermediate shape(s) can be altered in a series of post-processing operations to form a digital model of a corrective appliance; including "thickening," the creation of at least one retention post; an air hole and/or at least one nasal strut. Although each surface model can be viewed in three-dimensions, its surface has a zero thickness. The digital model is given a thickness. A second surface is created adjacent to the digital palatal model, e.g., by offsetting a copy of the surface in a caudad (inferior) or positive Z direction by a specified amount (e.g., 1/16", 2/16", 3/16", or 1/4"), depending on, inter alia, the rigidity of the material used to fabricate the corrective appliance.

FIGS. 4A-D show various views of an exemplary digital model of a corrective appliance 400 that is unitary and created to engage an early-shape (e.g., the initial, untreated shape) of a unilateral cleft palate. The corrective appliance 400 has a first region 402 that engages a first maxillary segment (e.g., a major maxillary segment 302), a second region 404 that engages a second maxillary segment (e.g., a minor maxillary segment 304), and a distance between the first region and the second region. FIGS. 4E-4H show various views of a digital model of a corrective appliance 410 that was created to engage a late-shape (e.g., the final shape) cleft palate. The distance in a corrective appliance adapted to engage a late-shape of a unilateral complete cleft palate will be less than a distance in a corrective appliance adapted to engage an early-shape of a cleft palate. This distance will progressively decrease in much the same fashion as the separation decreases between the maxillary segments in FIG. 3. Specifically, an appliance adapted to fit an early-shape palate will have a separation more similar to, for example, separation 300, separation 306, or separation 308; an appliance adapted to fit a late-shape palate will have a separation more similar to, for example, separation 332, separation 330, or separation 328; an appliance adapted to fit an intermediate-shape cleft palate will have a separation more similar to, for example, separation 316, separation 318, or separation 320. To illustrate further, FIG. 41 shows a superior view of the early-shape appliance 400 superimposed on the late-shape appliance 410.

The steps of alteration to a digital model of a cleft palate appliance can be performed in any order. At least one retention post 408 and/or an airway hole 406, and/or a nasal strut(s) 412 can be added; the model can be given a thickness; and any or all of the edges of the model can optionally be smoothed. FIGS. 4E-4H show a model of a late-shape appliance 410 in which the distance between the first major maxillary segment and the second minor maxillary segment can be much reduced compared to the separation in early-shape appliance 400. For example, the distance between the first and second maxillary segments of the final-stage appliance can be about 2 mm, whereas the distance between the first and second maxillary segments of the early-stage appliance can be about 15 mm.

In some embodiments, the digital model of a corrective appliance can be for a bilateral cleft palate or mid-line cleft palate and the steps of alteration of the corrective appliance can be designed accordingly. For example, for a bilateral cleft palate, the digital model can represent a structure (e.g., a unitary structure) that can have a first region designed to engage a first maxillary segment of a bilateral cleft palate, a second region designed to engage a second (e.g., contralateral) maxillary segment of a bilateral cleft palate, and a third region designed to engage the premaxilla. The first and the third regions are positioned at a first distance from one another, and the second and the third regions are positioned at a second distance from one another. Similar to the progression described above for the corrective appliance for a unilateral cleft palate, both the first distance and the second distance in the corrective appliance adapted to engage a late-shape of a bilateral cleft palate will be less than the corresponding distances in a corrective appliance adapted to engage an early-shape of a bilateral cleft palate.

Figure 4B:
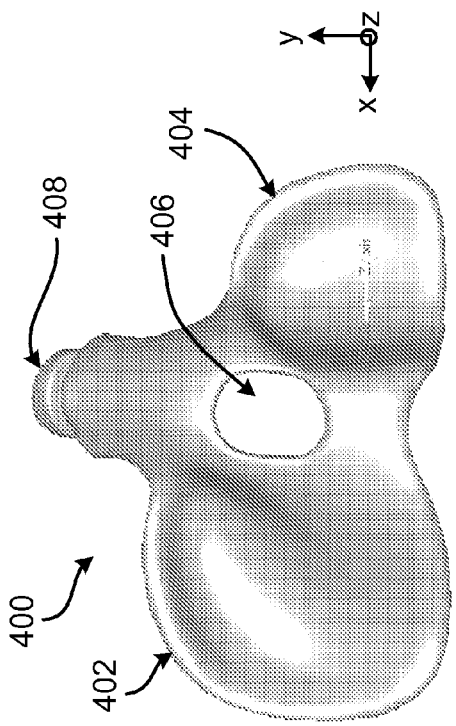
Figure 4D:
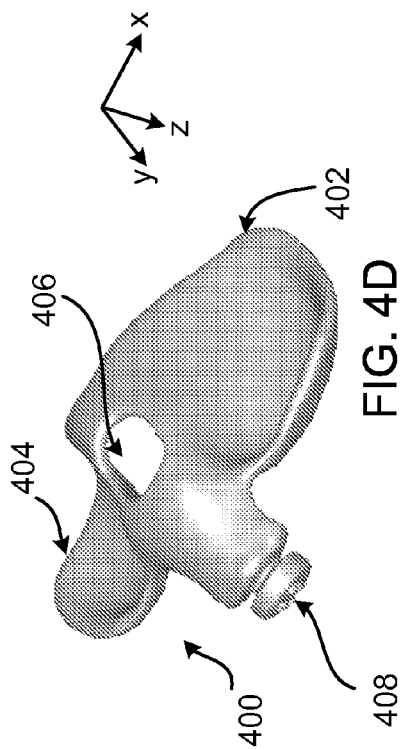
Figure 4A:
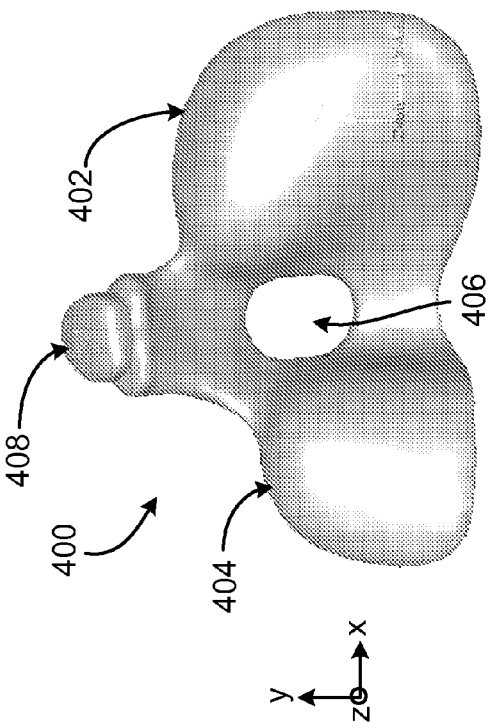
Figure 4C:
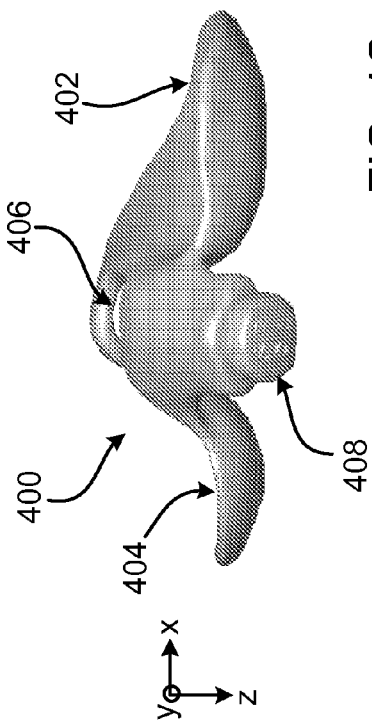
Figure 4I:
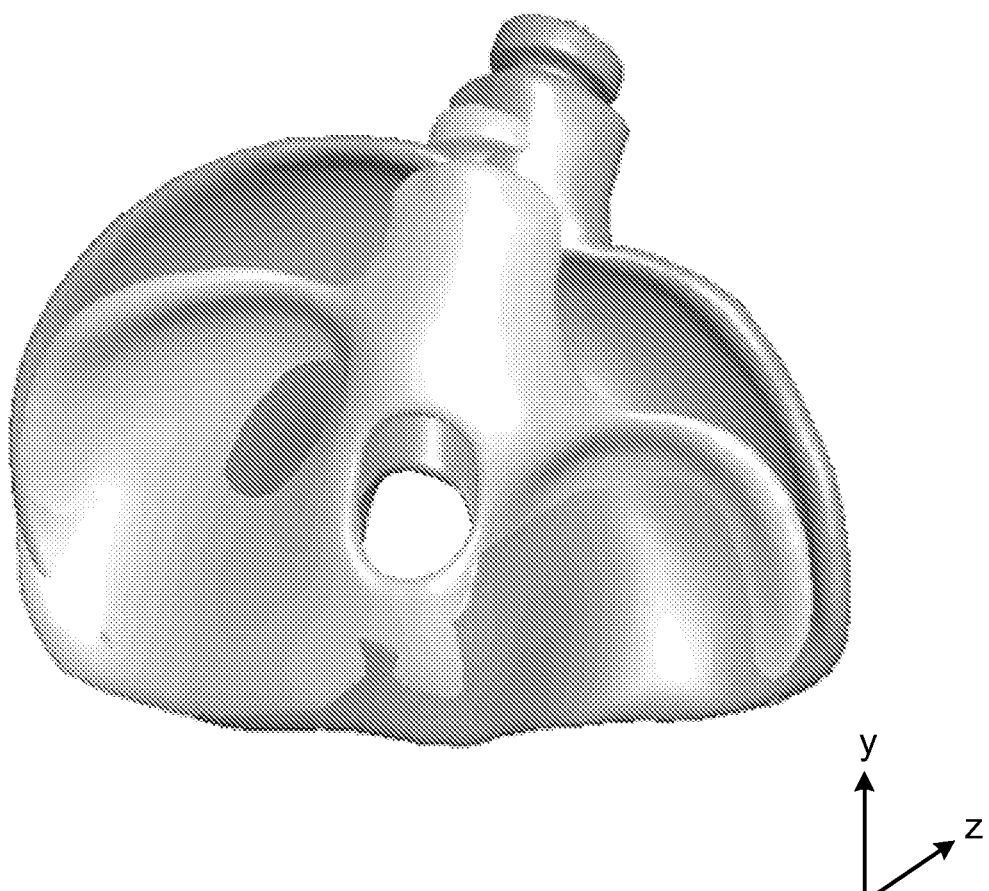
Figure 4J:
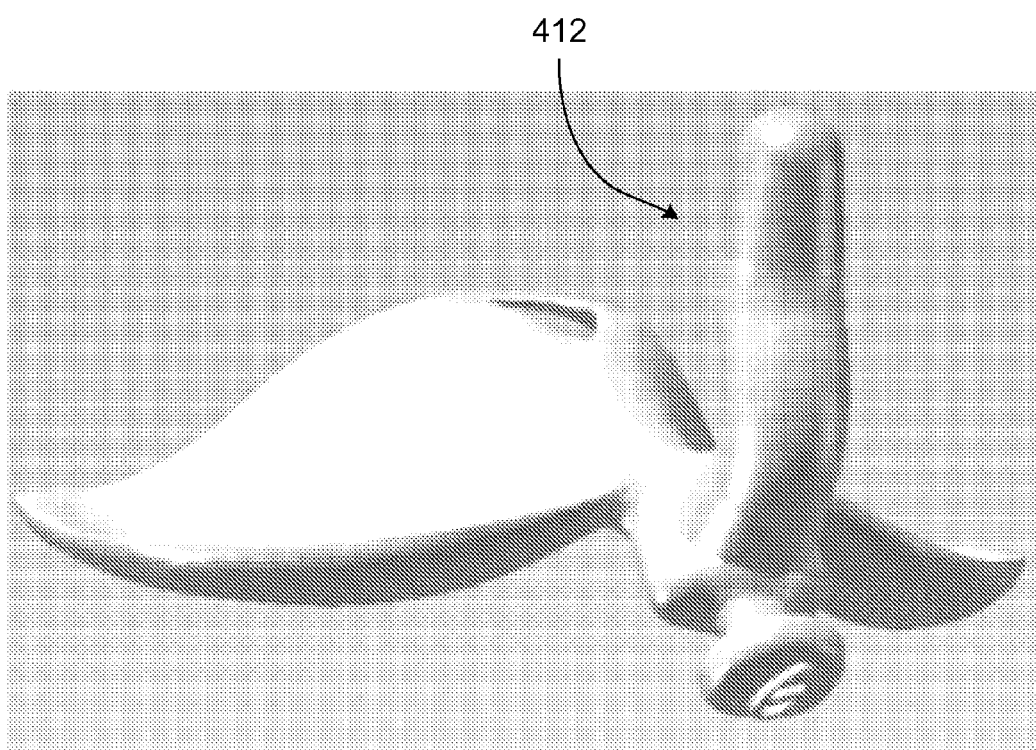

In some embodiments, strut(s) can be added to one or more digital models of corrective appliances, the position of which can be adjusted in each to correct a deformity (e.g., a flattened nostril or to elongate a short columella). FIG. 4J shows a digital model of an exemplary configuration of a corrective appliance comprising a nasal strut 412, i.e., an extension from the body of the corrective appliance positioned (e.g., at a forward end of the appliance, e.g., extending from a portion of the retention post) adapted to engage a patient's nasal ala while the patient is wearing the appliance.

Fabricating Corrective Appliances

In some instances, the digital models of one or more appliances can be written to a computer-readable medium in a format (e.g., STL or IGES) that is supported by a software used in a rapid prototyping technology (e.g., Selective Laser Sintering (SLS), stereolithography, 3D printing, or fused deposition modeling) or other means of automated fabrication (e.g. Computer-Numerically Controlled milling). Computer-readable media suitable for storing the digital models include all forms of volatile or non-volatile memory, media and memory devices, including, by way of example, flash memory devices, magnetic disks, e.g., internal hard disks or removable disks, magneto optical disks, CD ROM and DVD-ROM disks, magnetic tape, and other non-electronic forms of computer-readable media such as punched paper tape.

The digital models, e.g., on a computer-readable medium, can be used, e.g., by an internal or external manufacturing facility, to fabricate the initial shape, final shape and at least one (e.g., two, three, four, five, six, 12, 15, 18, or 20) corrective appliance in a prescribed series. The one or more (e.g., the entire series) corrective appliances can be created. These appliances can be fabricated using any material, e.g., nylon (e.g., Duraform PA™), photopolymer (e.g., DuPont Cyrel™, BASF Nyloflex™, Elaslon®, or McDermid), thermoplastic or resin (e.g., polyphenylene ether (PPE), polycarbonate (PC), or ethylene methacrylic acid), metal, ceramic, wax, or plaster, or any mixture of the aforementioned materials. Skilled practitioners will appreciate that any number of materials known in the art can be used and the choice of materials will depend on the intended application.

The appliances can be created using any methods known in the art, in a single production run (e.g., all at once) or in multiple production runs.

One or more appliance can be formed according to the geometry defined in the digital model using a machine that produces physical parts from three-dimensional digital models. For example, a rapid prototyping technology (e.g., Selective Laser Sintering, stereolithography, 3D printing, fused deposition modeling), or other means of automated manufacturing (e.g., Computer-Numerically Controlled milling) can be used to create one or more of the appliances.

In some embodiments, digital molds for the corrective appliances can be created by forming a negative digital model from the positive digital model of the appliance. A physical mold for the appliance then can be formed from the digital model by a method of three-dimensional construction known in the art. Material then can be added to the mold to create a corrective appliance conforming to the dimensions of one or more of the physical models. The articles so formed, if necessary, can be cooled to set the shape and induce crystallization.

U.S. Pat. No. 5,866,058, which is incorporated by reference, describes rapid prototyping of models, including the making of three-dimensional, solid objects in accordance with a specified design, with the design usually comprising mathematical data from a three-dimensional, computer-aided design system or solid modeling system. Rapid prototyping systems can create physical objects by a technique, e.g., a sequential photopolymerization of layers of a monomer, a laser fusing of particulate, a sequential extrusion of a thermoplastic, a lamination of scribed layers of paper, a thermal jetting of solidifiable wax or metal, a laser-enhanced chemical vapor deposition, a brazing together of pre-machined plates, a jetting of binder onto ceramic powders, or any combination of the aforementioned steps known to skilled practitioners. In one rapid prototyping system of creating solid models by depositing thermally-solidifiable materials, a flowable material is sequentially deposited on a seed, a substrate, or on previously-deposited thermoplastic material. The material solidifies after it is deposited and is thus able to incrementally create a desired form. Examples of thermally-solidifiable systems include fused-deposition modeling, wax jetting, metal jetting, consumable rod-arc welding, and plasma spraying. Alternatively or in addition, other means of automated fabrication (e.g. Computer-Numerically Controlled milling) can be used.

While in a molten condition, the material chosen to construct the appliance can be processed into the desired shape using any known technique, e.g., extrusion, injection molding, compression molding, blow molding, film blowing, fiber spinning, blown fiber, spunbonded fiber coextrusion, paper coating, calendering, rotational molding, casting, or thermoforming.

A skilled practitioner would appreciate the variety of manufacturing techniques materials known in the art for constructing medical appliances and molds for medical appliances.

Corrective Appliances

A digital model of a corrective appliance (e.g., appliance 400 or 410) or a physical corrective appliance can be a unitary structure that, when treating, for example, a unilateral complete cleft palate, can have a first region designed to engage a first maxillary segment (e.g., major maxillary segment 302) and a second region designed to engage a second maxillary segment (e.g., minor maxillary segment 304). The first and the second regions are positioned at a distance, e.g., from one another, similar to any of the distances shown in FIG. 3 (e.g., separation 300, separation 314, or separation 332) between maxillary segments 302 and 304.

The general appearance of a physical corrective appliance can be similar to the digital model of the corrective appliances shown in FIG. 4A-4J and can be measured using the same spatial axes. The first region of the physical appliance is similar in appearance to the first region 402 of the digital model; the second region of the physical appliance is similar in appearance to the second region 404 of the digital model. In this example, the corrective appliance is designed to be inserted into the mouth of the patient such that the most superior aspect of the appliance is closest to the most caudad aspect of the patient's palate. When the appliance is inserted into the patient's mouth in this manner, the first region 402 will cup a first maxillary segment (major maxillary segment 302) and the second region 404 will cup a second maxillary segment (minor maxillary segment 304).

The digital model of a corrective appliance as well as the physical corrective appliance itself can be designed to be appropriate for the treatment of a bilateral complete cleft palate. For example, the corrective appliance can be a unitary structure that has a first region designed to engage a first maxillary segment, a second region designed to engage the contralateral maxillary segment, and a third region designed to engage the premaxilla. The first and the third regions can be positioned (e.g., based on a patient's anatomy) at a first distance from one another, and the second and the third regions can be positioned at a second distance from one another.

An appliance can be designed to allow air to flow through itself. In the event the appliance were to become dislodged, the appliance would allow air to flow into the patient's airway, precluding obstruction. For example, an appliance can include an airway hole(s). An airway hole of a corrective appliance can be similar in form to the airway hole 406, shown in FIG. 4A. An airway hole can be of any geometrical shape (e.g., a circle, a square, or an oval). The airway hole can be of any size or any shape conducive to air flow.

An appliance can include one or more retention posts. The retention post of the corrective appliance can be similar in form to the retention post 408 of the digital model, shown in FIG. 4A. The retention post can have a smooth and non-indented geometry. The end of the retention post can be any geometrical shape (e.g., a circle, a square, or an oval). Optionally, the end of the retention post can be engraved with information (e.g., a patient identification number, a set of patient initials, or a sequence number or letters of the appliance that indicates the order in which the appliance is to be administered). The corrective appliance can be inserted or removed from the patient's mouth, for example, by grasping the retention post.

Optionally, dental elastics can be attached to the corrective device (e.g., affixed to a groove at the end of the retention post). The dental elastics can be taped to the patient's cheeks using Steri-Strips™ (or similar adhesive material) and provide a primary means of retaining the corrective appliance in the patient's mouth. Additional retention forces can be provided by the tongue and lower jaw of the patient when the mouth is in a closed position. In some instances, no dental elastics are used, and the appliance is kept in place by the patient (e.g., by a sucking force applied by the patient).

In some embodiments, the more dorsal segment connecting the first and second regions of the corrective appliance can be omitted. Such an omission would enlarge the dorsal aspect of the region described as an airway hole.

Optionally, one or more struts, e.g., with a bulbous end can extend from the base of the appliance and can be inserted into, for example, a nostril, or the nostrils, of the patient. Such an arrangement can be used for example, to correct a flattened nostril or to elongate a short columella, which can be characteristic of a unilateral and bilateral complete cleft palate.

Optionally, any or all edges of the appliance can be smoothed to ensure a comfortable fit for the patient. The smoothing can be performed by editing appropriately the digital model or by manually editing (e.g., removing material from) the physical appliances or both. The corrective appliance can be made of e.g., methyl methacrylate, nylon, photopolymer (e.g., DuPont Cyrel™, BASF Nyloflex™, Elaslon®, or McDermid), thermoplastic or resin (e.g., polyphenylene ether (PPE), polycarbonate (PC), or ethylene methacrylic acid), metal, ceramic, wax, plaster, mixtures thereof, or other material.

In some embodiments, a property (e.g., reactivity, water resistance, softness, durability, or toxicity) of the appliance can be improved by coating the appliance with an appropriate material (e.g., a sealant). The coating can be applied thinly so that it would not interfere with the fit of the appliance. Alternatively or in addition, the coating thickness can be incorporated into the design of the corrective appliance (e.g., a size of the appliance can be reduced to compensate for a coating, subsequently applied, having a specific thickness).

A patient can be treated sequentially, e.g., using the initial shape, final shape and at least one constructed corrective appliances that each correspond to a separate maxillary separation in the corrective process. The distance between the first and second regions in the corrective appliance corresponding to a later stage in the corrective process is less than the distance between the first and second regions in the corrective appliance corresponding to an earlier stage in the corrective process. In the embodiment in which the initial shape, final shape and at least one corrective appliances are used, one appliance can be constructed in a geometry that reflects the initial, greater distance between the maxillary segments of a cleft palate patient. Another appliance can be constructed in a geometry that reflects a lesser separation between the maxillary segments. In the embodiment in which more than two (e.g., three, five, 10, 12, 15, 18, or 20) corrective appliances are used in a specified temporal sequence, subsequent appliances can be constructed in a geometry that reflects a progressively narrower gap between the maxillary segments or between each maxillary segment and the premaxilla, a larger overall size due to growth, and/or improved nostril configuration, than in earlier appliances.

Kits of Corrective Appliances

Also provided herein are kits for use by patients or practitioners or both. A kit can include, e.g., two three or more (e.g., 2, 3, 4, 5, 6, 10, 12, 15, 18, 20, or more) corrective appliances described herein, optionally with informational material. The informational material can be descriptive, instructional, marketing or other material that relates to the methods described herein. For example, the informational material can relate to the use (e.g., daily insertion, removal, lip taping, or cleaning) of a corrective appliance.

Kits can include accessories (e.g., orthodontic elastics, tape, Steri-Strips™ Tagaderm™, Duoderm™, or cleaning supplies) to be used with the appliances. Kits can also include one or more containers for the two or more corrective appliances. Kits can contain separate containers, dividers or compartments for the corrective appliances and informational material. Kits can include a plurality (e.g., a pack) of individual containers, each containing one or more corrective appliance. The containers of the kits can be air tight, or waterproof, or both and the containers can be labeled for a particular sequence of use. For example, a container can be labeled with a number instructing in which order the corrective appliance should be used for the pre-surgical treatment of cleft palate.

Treating Cleft Palate with Corrective Appliances

A patient may be treated using one or more of the methods, appliances, or kits described in this application using the following, exemplary steps.

A skilled practitioner obtains a three-dimensional model of the patient's palate. For example, a health care provider can make a palatal impression of the patient's palate and form a plaster model from the impression. As a means of checking the accuracy of this model, a clear plastic plate can be formed over the plaster model using a thermoplastic or other suitable material. The practitioner can test the fit of the plastic model on the patient and can make any adjustments necessary for a better custom fit. Following any modifications to this plastic plate, another plaster model can be created from the adjusted test plate. The surface anatomy of the finalized plaster model can be captured using a three-dimensional scanner. Alternatively or in addition, one may scan the palatal impression of the patient's palate directly.

Alternatively or in addition, a three-dimensional model of the patient's palate can be obtained, e.g., by using a series of two-dimensional biomedical imaging scans (e.g., magnetic resonance imaging, computed tomography, or intraoral scanning), by using one three-dimensional biomedical imaging scan, or by using a reconstruction based on the two- or three-dimensional scans.

Data representative of the three-dimensional structure of the cleft palate (e.g., a point cloud representative of the physical model of the palate, an IGES file, a DICOM file of the tomography of the patient's palate, or a reconstruction of the patient's palate based on a DICOM file) can be transferred, for example, from the scanner into a commercially-available software package (e.g., AutoCAD®, Geomagic Studio®, SolidWorks® or TurboCAD®)

The software package can be used to construct a digital model of the palate from the obtained data (e.g., a point cloud, a DICOM file, or a reconstruction from a DICOM file) that represents the initial shape of the palate. The digital model can be edited to bring the separate alveolar (gum) segments together to narrow the cleft, while also allowing for growth to occur. Digital models of maxillary segments can be manipulated to achieve an ideal dental arch configuration, i.e., the final palate topography. The digital model of the final palate shape can be scaled to account for anticipated growth during a planned duration of treatment (e.g., two months, four months, or six months).

By interpolating between the initial and the final digital models, an appropriate number of digital intermediate models (e.g., two, four, six, eight, 10, 12, 15, or more) can be made to achieve the final alveolar configuration. These digital palate models can represent the gradual, physical, three-dimensional narrowing of the palatal cleft or clefts during therapy in the growing patient. In some embodiments, each digital palate model can be altered in a series of steps to form a digital model of an appliance. The digital palate model can be given a thickness; a surface can be formed adjacent to the inferior palatal surface. Additional steps, one or more of which can be performed in any order, can include: adding an airway hole; adding a retention post; smoothing one or more edges of the adjacent model, adding a nasal strut(s), et al.

The digital models of the series of appliances can be written to a computer-readable medium in a format (e.g., STL or IGES) that is supported by a software used in a rapid prototyping technology (e.g., Selective Laser Sintering, stereolithography, 3D printing, or fused deposition modeling) or other means of automated fabrication (e.g. Computer-Numerically Controlled milling). Computer-readable media suitable for storing the digital models include all forms of volatile or non-volatile memory, media and memory devices, including, by way of example, flash memory devices, magnetic disks, e.g., internal hard disks or removable disks, magneto optical disks, CD ROM and DVD-ROM disks, magnetic tape, and other non-electronic forms of computer-readable media such as punched paper tape.

The digital models, e.g., on a computer-readable medium, can be used, e.g., by an internal or external manufacturing facility, to fabricate at least one (e.g., two, three, four, five, six, 12, 15, 18, or 20) corrective appliance in a prescribed series. The one or more (e.g., the entire series), corrective appliances can be created. These appliances can be fabricated using any material, e.g., methyl methacrylate, nylon (e.g., Duraform PA™) photopolymer (e.g., DuPont Cyrel™, BASF Nyloflex™, Elaslon®, or McDermid), thermoplastic or resin (e.g., polyphenylene ether (PPE), polycarbonate (PC), or ethylene methacrylic acid), metal, ceramic, wax, or plaster, or any mixture of the aforementioned materials.

A skilled practitioner would appreciate the variety of manufacturing techniques and materials known in the art for constructing medical appliances and molds for medical appliances. The appliances can be created, using any methods known in the art, in a single production run (e.g., all at once) or in multiple production runs.

In some embodiments, one or more of the appliances can be formed in the geometry defined in the digital model by using a machine that produces physical parts from three-dimensional digital models. For example, a rapid prototyping technology (e.g., Selective Laser Sintering, stereolithography, 3D printing, or fused deposition modeling), or other means of automated manufacturing (e.g., Computer-Numerically Controlled milling) can be used to create one or more of the appliances.

In some embodiments, digital molds for the appliances can be created by forming a negative digital model that engages the positive digital model of the appliance. A physical mold for the appliance then can be formed from the digital model by a method of three-dimensional construction known in the art. Material can be added to the mold to create a corrective appliance conforming to the dimensions of one or more of the digital models.

Figures 5A, 5B:
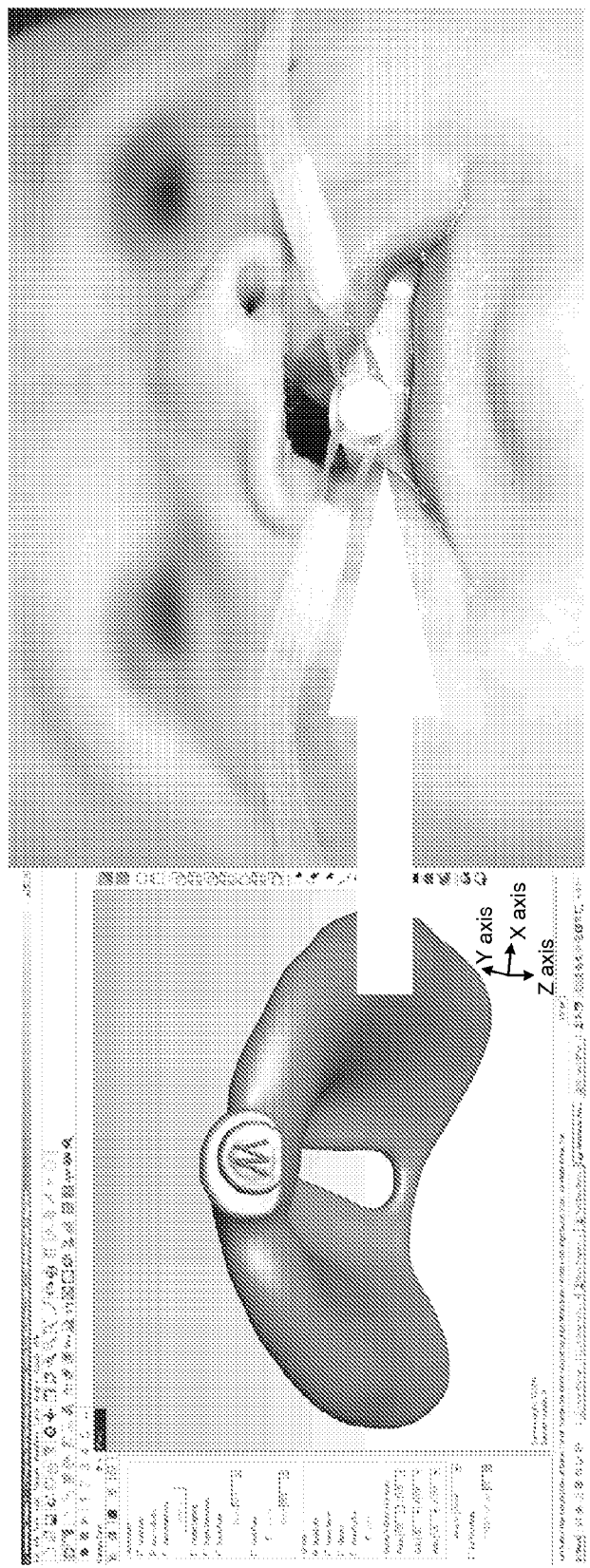
FIGS. 5A-5B illustrate an exemplary mode of securing an appliance described herein to a patient.

Appliances can be administered to the patient by any person, e.g., a parent of a patient or a health care provider. The appliance can be secured to the patient using any method known in the art, e.g., using elastics and/or adhesives. An exemplary mode of securing an appliance described herein to a patient is illustrated in FIGS. 5A and 5B, where the corrective appliance is secured to the patient with elastic bands and adhesive tape. The patient wears each appliance for a specified time (e.g., two days, seven days, 10 days, 14 days, or more), during which, for example, the distance between the first major maxillary segment and the second minor maxillary segment is reduced. In some bilateral embodiments, during the treatment period, the distance between each maxillary segment and the premaxilla will be reduced. During or after the specified time, the patient can receive the next appliance in the series. The patient can also undergo additional evaluation, e.g., a health care provider can examine the patient to assess, one or more of e.g., cleft closure, physical growth of a maxillary bone, gum irritation, cheek skin integrity, or ability to feed while wearing an appliance. In addition, the health care provider can examine the corrective appliance to assess the durability of the appliance fasteners, the cleanliness of the appliance, or both.

Upon completion of a course of therapy, the distance between, for example, the maxillary segments or between each maxillary segment and the premaxilla can be reduced (e.g., to a distance specified by a health care provider), and the child can undergo lip repair surgery.

In some embodiments, treatment can be provided after lip repair but before palate repair. A tension of the repaired lip can have an inhibiting effect on the forward growth of the cleft maxilla. Continued treatment of patients with a corrective appliance after lip-repair surgery could reduce the growth-inhibiting effect of the tension of the repaired lip. The growth of the maxilla can be considered when designing the corrective appliance.

In some embodiments, further treatment using the methods described herein can be provided after palate repair.

Some patients can develop "alveolar collapse" after palate repair, in which the medial positioning of the anterior portion of the minor alveolar segment is located behind the premaxilla. This condition disrupts the normal dental arch and can be induced by, for example, the contracture of the scar from the palate repair, or a premature lip repair. Patients with alveolar collapse can be treated with a palatal expander device, which can be fixed in the roof of the mouth and can be adjusted by a health care provider. The continued wear (e.g., after palate repair) of appliances as described herein may prevent alveolar collapse, while continuing to allow for growth of the maxilla.

Skilled practitioners will appreciate any number of variations may be included that are known in the field to diagnose and to treat patients with cleft palate.

Implementation

Implementation of the subject matter and the functional operations described in this specification can be performed in digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a computer readable medium for execution by or to control the operation of a data processing apparatus.

The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to a suitable receiver apparatus.

A computer program (often referred to as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical, or optical disks. However, a computer need not have such devices.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

EXAMPLE 1

Treatment of a Patient's Unilateral Cleft Palate

Figure 6C:
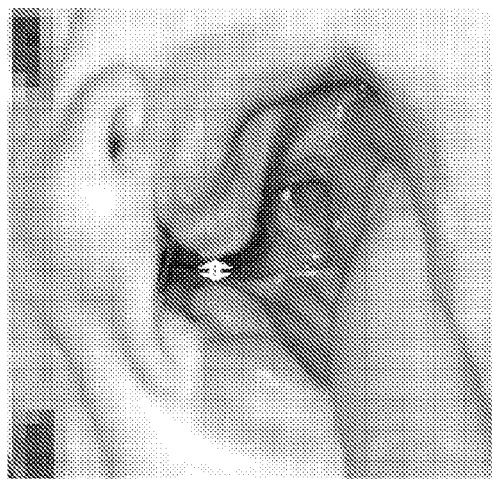
FIGS. 6A-6C are photographs of a patient undergoing treatment using methods described herein.
Figure 6B:
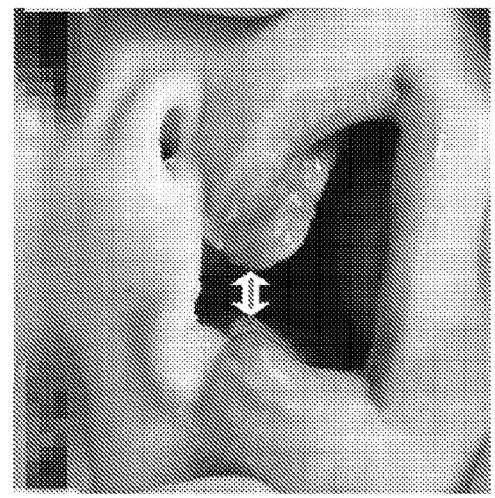
Figure 6A:
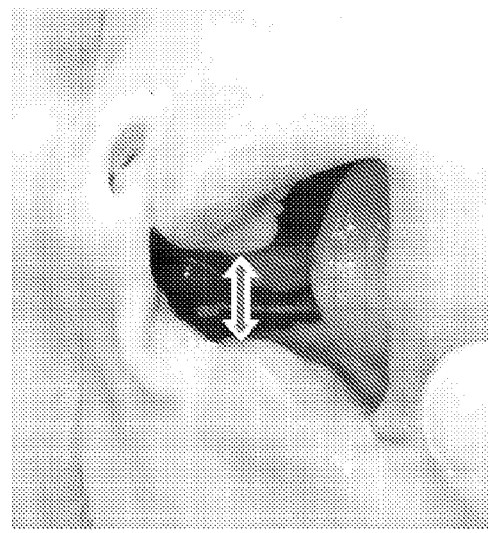
Figure 7A:
FIGS. 7A-7B are photographs of a patient who underwent treatment using methods described herein, followed by lip repair surgery.
Figure 7B:

A number of patients were treated using the methods described herein. Briefly, for each patient, an impression was taken of the patient's palate using a commercially-available dental impression material. A plaster positive model of the palate was formed. This was scanned and a three-dimensional model of the initial palate shape was created. The three-dimensional model of the initial palate shape was edited to create a digital model of the desired final shape of the palate, taking into account the expected growth of the patient's palate during the treatment period. Ten intermediate shapes were created based on the models of the initial and final shapes of the palate. Digital models of corrective appliances designed to engage the initial, intermediate and final shapes of the patient's cleft palate were created. Corrective appliances were fabricated based on the digital models of the corrective appliances using DuraForm™ PA by Rapid Prototpying. The first corrective appliance in the series, i.e., the appliance adapted to fit the initial shape of the cleft palate, was applied to the patient using elastic bands and adhesive tape as shown in FIG. 5B. Each appliance was worn by the patient for one week for a total treatment period of twelve weeks. FIGS. 6A-6C are photographs of one patient who has undergone the treatment. FIG. 6A shows the patient's cleft palate prior to treatment (e.g., with an initial shape of the cleft palate). FIG. 6B shows the patient's cleft palate at an intermediate stage of treatment. FIG. 6C shows the patient's cleft palate at a later stage of treatment. The treatment was followed by lip reconstructive surgery. The final results of treatment of one patient are shown in FIG. 7A, which is a photograph of the patient five days after surgery, and 7B, which is a photograph of the patient two weeks after surgery.

A number of embodiments of the invention have been described. Nevertheless, it will be understood that various modifications may be made without departing from the spirit and scope of the invention. Accordingly, other embodiments are within the scope of the following claims.

What is claimed is:

1. A group of corrective appliances, each adapted to engage a shape of a unilateral cleft palate and each comprising:
   (a) a first region that engages a major maxillary segment of the cleft palate; and
   (b) a second region that engages a minor maxillary segment of the cleft palate, wherein the first and the second regions are separated by a distance and the distance in any one appliance in the group is different from the distance in any other appliance in the group.

2. The group of corrective appliances of claim 1, wherein at least one appliance is formed of a material comprising nylon.

3. The group of corrective appliances of claim 1, wherein at least one appliance is formed of a material comprising methyl methacrylate.

4. A group of corrective appliances, each adapted to engage a shape of a bilateral cleft palate and each comprising:
   (a) a first region that engages a first maxillary segment of the cleft palate;
   (b) a second region that engages a second maxillary segment of the cleft palate; and
   (c) a third region that engages a premaxilla of the cleft palate, wherein the first region and the premaxilla are separated by a first distance and the second region and the premaxilla are separated by a second distance and at least one distance in any one appliance in the group is different from at least one distance in any other appliance in the group.

5. The group of corrective appliances of claim 4, wherein at least one appliance is formed of a material comprising nylon.

6. The group of corrective appliances of claim 4, wherein at least one appliance is formed of a material comprising methyl methacrylate.

7. A kit comprising at least two corrective appliances, each appliance comprising:
   (a) a first region configured to engage a major maxillary segment of a unilateral cleft palate; and
   (b) a second region configured to engage a minor maxillary segment of a unilateral cleft palate, wherein the first and the second regions are separated by a distance and the distance in any one appliance in the kit is different from the distance in any other appliance in the kit.

8. The kit of claim 7, wherein at least one appliance is formed of a material comprising nylon.

9. The kit of claim 7, wherein at least one appliance is formed of a material comprising methyl methacrylate.

10. A kit comprising at least two corrective appliances, each appliance comprising:
    (a) a first region that engages a first maxillary segment of bilateral cleft palate;
    (b) a second region that engages a second maxillary segment of a bilateral cleft palate; and
    (c) a third region that engages a premaxilla of the bilateral cleft palate, wherein the first region and the premaxilla are separated by a first distance and the second region and the premaxilla are separated by a second distance and wherein at least one distance in any one appliance in the kit is different from a at least one distance in any other appliance in the kit.

11. The kit of claim 10, wherein at least one appliance is formed of a material comprising nylon.

12. The kit of claim 10, wherein at least one appliance is formed of a material comprising methyl methacrylate.

* * * * *

UNITED STATES PATENT AND TRADEMARK OFFICE
CERTIFICATE OF CORRECTION

| | | |
|---|---|---|
| PATENT NO. | : 8,768,497 B2 | Page 1 of 1 |
| APPLICATION NO. | : 12/867171 | |
| DATED | : July 1, 2014 | |
| INVENTOR(S) | : Philip B. Stoddard and Beth A. Roscoe | |

It is certified that error appears in the above-identified patent and that said Letters Patent is hereby corrected as shown below:

In the Claims:

Col. 20, line 49, Claim 10, delete "a at" and insert -- at --.

Signed and Sealed this
Sixteenth Day of September, 2014

Michelle K. Lee
*Deputy Director of the United States Patent and Trademark Office*